United States Patent
Horii et al.

(10) Patent No.: US 11,713,440 B2
(45) Date of Patent: Aug. 1, 2023

(54) CELL CULTURE SYSTEM AND CELL CULTURE DEVICE

(71) Applicant: Sinfonia Technology Co., Ltd., Tokyo (JP)

(72) Inventors: Daichi Horii, Tokyo (JP); Kazuhiro Tsuji, Tokyo (JP); Yoshihiko Nishikawa, Tokyo (JP); Haruki Takeuchi, Tokyo (JP)

(73) Assignee: Sinfonia Technology Co., Ltd., Tokyo (JP)

( * ) Notice: Subject to any disclaimer, the term of this patent is extended or adjusted under 35 U.S.C. 154(b) by 227 days.

(21) Appl. No.: 16/723,416

(22) Filed: Dec. 20, 2019

(65) Prior Publication Data
US 2020/0208087 A1      Jul. 2, 2020

(30) Foreign Application Priority Data

Dec. 28, 2018   (JP) ................................. 2018-248031

(51) Int. Cl.
*C12M 1/12* (2006.01)
*C12M 3/04* (2006.01)
(Continued)

(52) U.S. Cl.
CPC ............ *C12M 23/04* (2013.01); *C12M 27/10* (2013.01); *C12M 33/00* (2013.01); *C12M 41/48* (2013.01)

(58) Field of Classification Search
CPC ...... C12M 23/04; C12M 27/10; C12M 33/00; C12M 41/48
See application file for complete search history.

(56) References Cited

U.S. PATENT DOCUMENTS 3,847,749 A * 11/1974 Smith ................... C12M 29/00
                                                            435/308.1
5,265,822 A * 11/1993 Shober, Jr. .......... A61M 5/1418
                                                            242/388.2
(Continued)

FOREIGN PATENT DOCUMENTS

EP          3255137 A1     12/2017
JP       2014-233252    * 12/2014  .............. C12M 1/00
(Continued)

OTHER PUBLICATIONS

Machine Translation of JP 2014-233252 (Year: 2021).*
Europe Patent Application No. 19217123.9, Search Report dated Aug. 14, 2020, 11 pages.
Exhibit No. Ko-3: Screenshots of Video from You Tube published on Sep. 9, 2018 ("Thermo Scientific Nunc Automatic Cell Factory Manipulator System: Product Overview").
(Continued)

*Primary Examiner* — William H. Beisner
*Assistant Examiner* — Danielle B Henkel
(74) *Attorney, Agent, or Firm* — Kilpatrick Townsend & Stockton LLP

(57) ABSTRACT

According to one embodiment of the present disclosure, a cell culture system includes: a cell culture container; a liquid storage part configured to store a liquid including a culture medium or a reagent to be supplied to the cell culture container; and a cell collection part configured to collect cells cultured in the cell culture container, wherein the cell culture container, the liquid storage part, and the cell collection part are connected by spatially closed-system lines at least during a period from feeding of the liquid to the cell culture container to removal of the cultured cells, and wherein the cell culture container is arranged in an incubator in a form of a multistage shelf including a liquid supply/discharge port.

6 Claims, 15 Drawing Sheets

(51) Int. Cl.
*C12M 1/26* (2006.01)
*C12M 1/36* (2006.01)

(56) References Cited

U.S. PATENT DOCUMENTS

| | | | | |
|---|---|---|---|---|
| 6,066,497 | A * | 5/2000 | Powell | C12M 29/04 |
| | | | | 435/298.2 |
| 2002/0045252 | A1* | 4/2002 | Yamashita | C12M 25/00 |
| | | | | 435/325 |
| 2003/0054335 | A1* | 3/2003 | Taya | C12M 41/36 |
| | | | | 435/325 |
| 2007/0065933 | A1* | 3/2007 | Esser | C12M 23/48 |
| | | | | 435/286.6 |
| 2021/0207073 | A1* | 7/2021 | Tanabe | C12M 25/06 |

FOREIGN PATENT DOCUMENTS

| | | | | |
|---|---|---|---|---|
| JP | 2018-139615 | * | 9/2018 | C12M 1/00 |
| JP | 2018138056 | | 9/2018 | |
| WO | 2017032829 A1 | | 3/2017 | |

OTHER PUBLICATIONS

Reference 2: Webpage introducing the automatic culture system for stem cells "Cellaforte" of NIPRO Corporation (publication date: Apr. 1, 2016).

Japanese Patent Application No. 2018-248031, Submission of Publications, etc., Mar. 4, 2022.

* cited by examiner

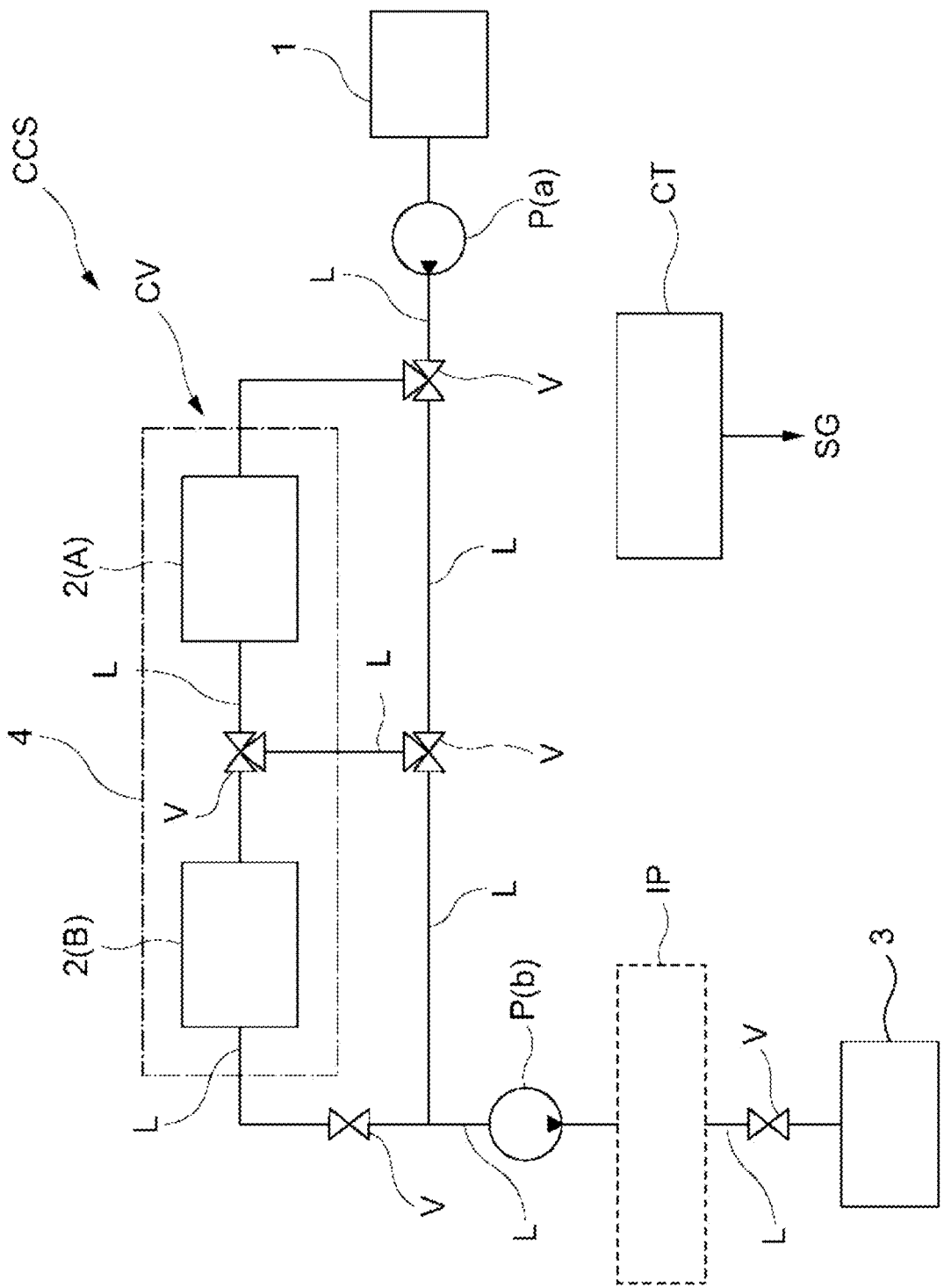

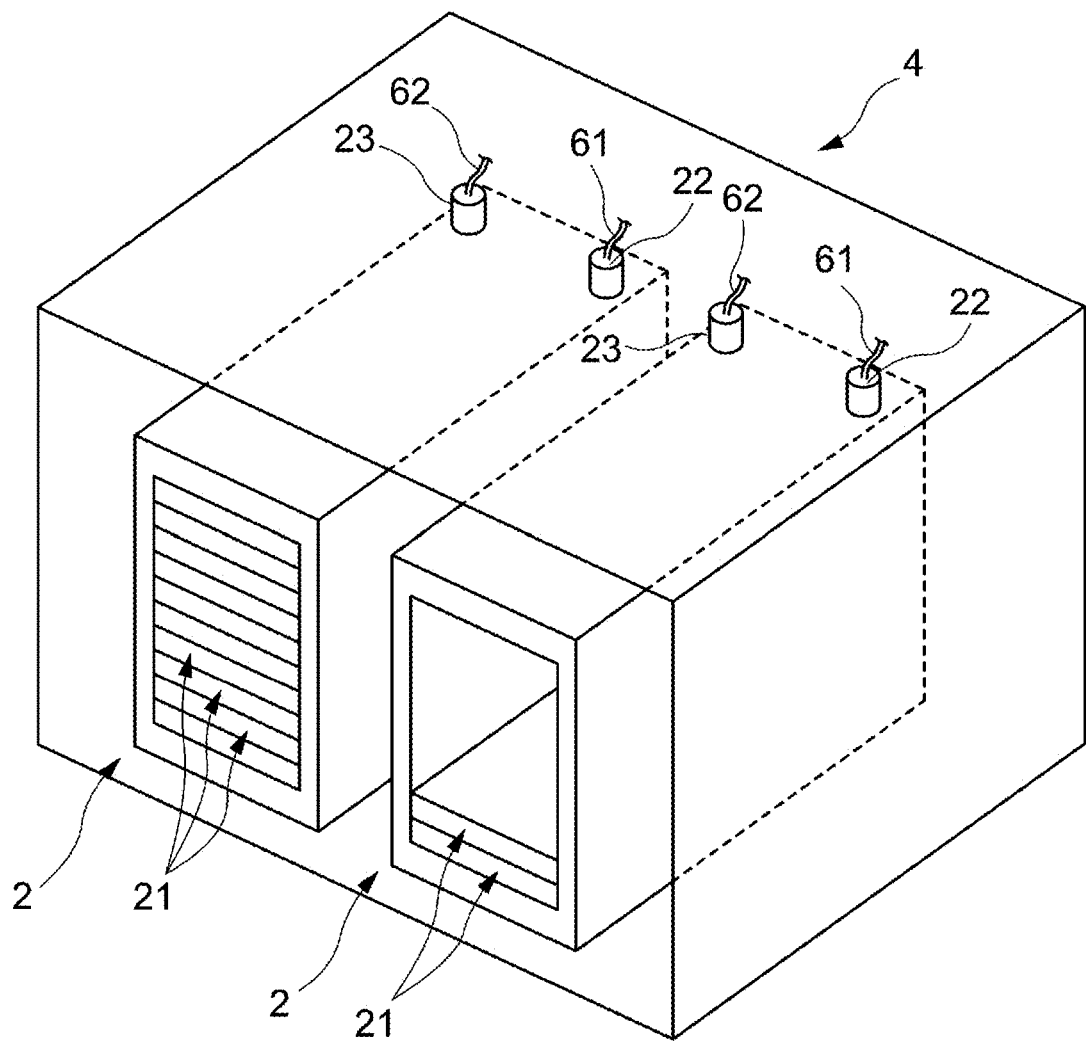

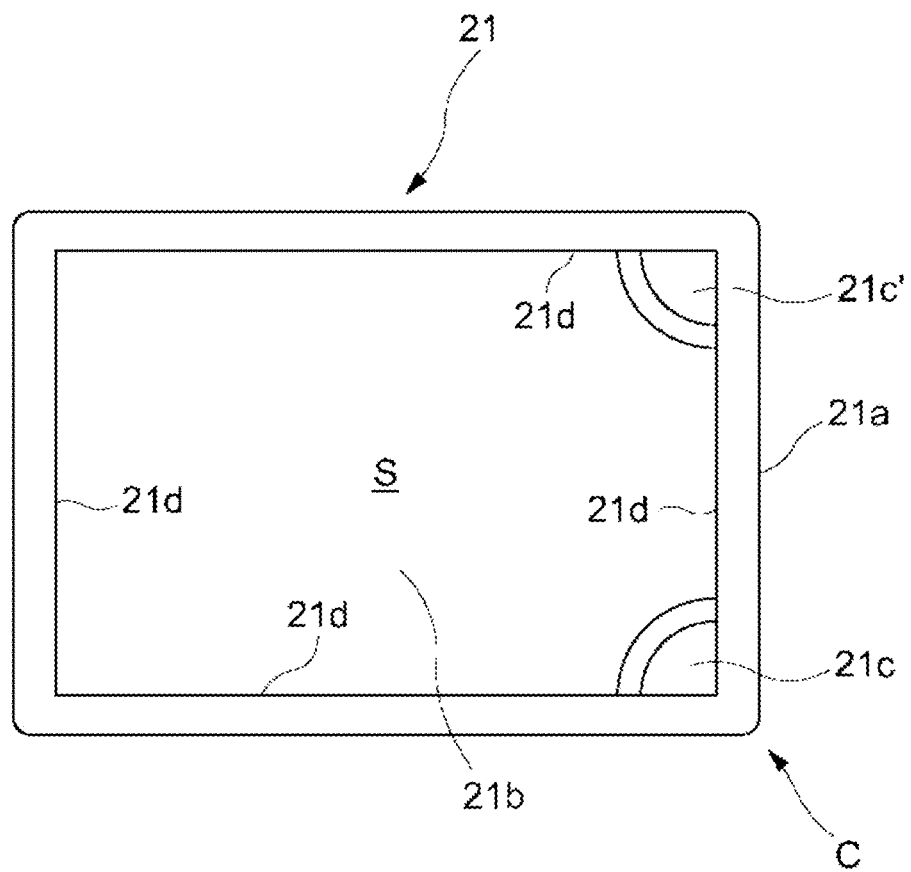

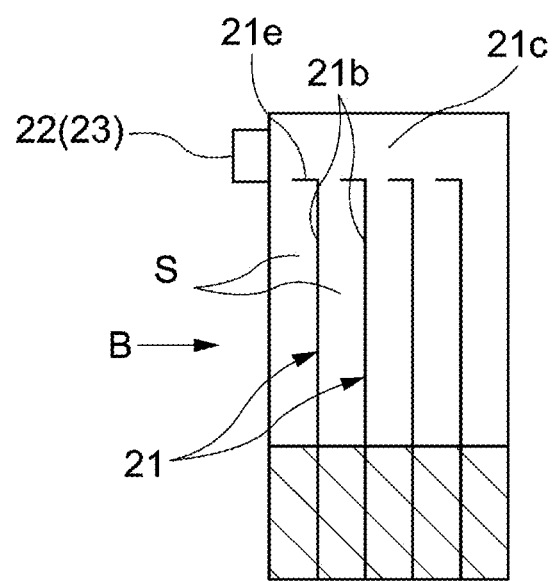

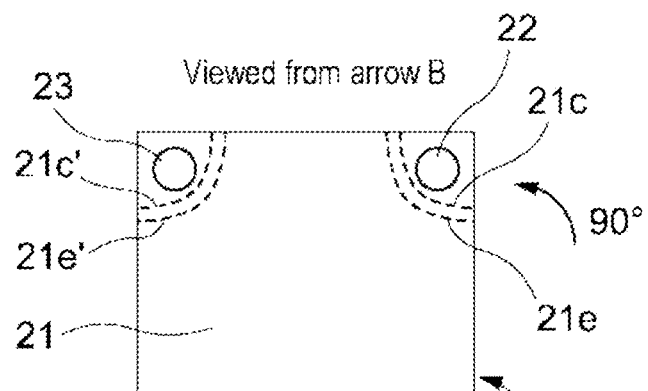
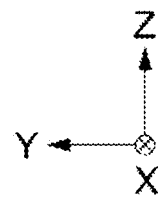

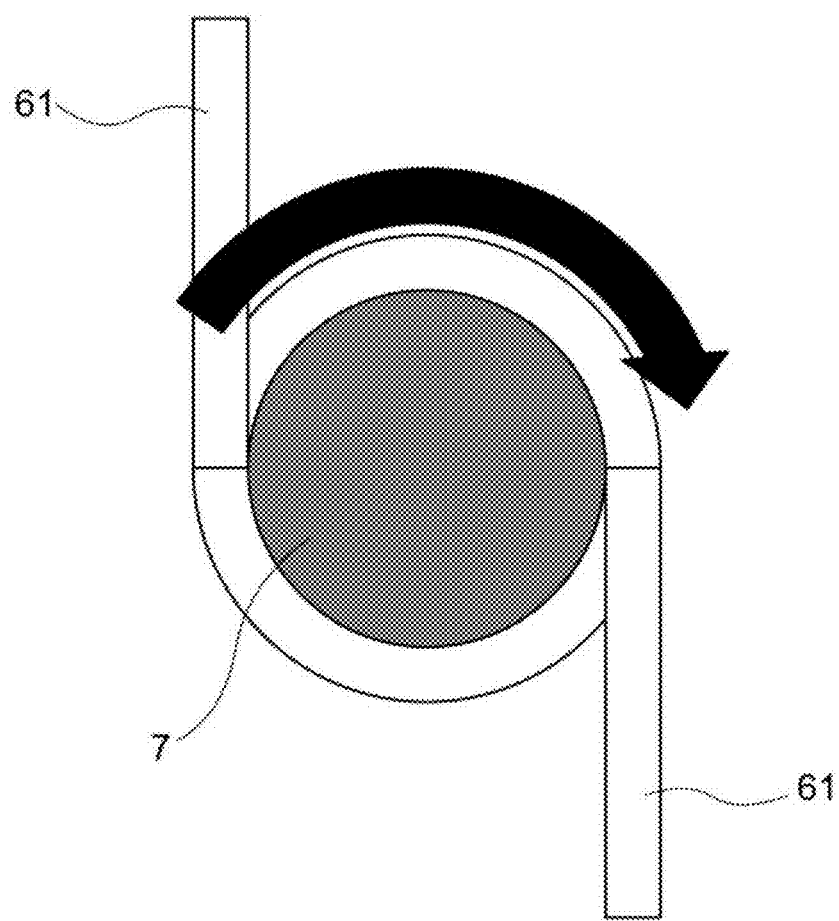

ND CELL
CELL CULTURE SYSTEM AND CELL CULTURE DEVICE

CROSS-REFERENCE TO RELATED APPLICATION

This application is based upon and claims the benefit of priority from Japanese Patent Application No. 2018-248031, filed on Dec. 28, 2018, the entire contents of which are incorporated herein by reference.

TECHNICAL FIELD

The present disclosure relates to a cell culture system and a cell culture device that are suitable for simply and appropriately performing mass culture.

BACKGROUND

In recent years, in order to culture a large amount of cells, there is known a cell culture technique for culturing cells seeded in a culture solution using a cell culture container having a multilayer structure containing a plurality of trays. In such a cell culture technique, in order to alleviate the burden on an operator, a cell culture device that performs a handling operation of holding and rotating a cell culture container is used to introduce a culture solution having seeded cells into the cell culture container or to recover the culture solution from the cell culture container (see Patent Document 1).

There is available a cell culture system that includes a carriage device capable of mounting and moving a multilayer type cell culture container containing a plurality of trays, and an operation device capable of holding and rotating the cell culture container. The carriage device includes a carriage having wheels, and a fixing member detachably mounted on the carriage to fix the cell culture container to the carriage. The operation device includes a rotation part for holding the cell culture container together with the fixing member and performing a rotation operation of rotating the cell culture container with a first rotation shaft and/or a second rotation shaft.

When the cell culture is finished, the cell culture container is removed from the operation device and is transferred to another place together with the carriage to collect cells. Next, a suspension of cells to be cultured and a culture medium is put into a cell culture container. The cell culture container is moved again by the carriage and is set in the operation device.

PRIOR ART DOCUMENT

Patent Document

Patent Document 1: Japanese Patent Application Publication No. 2018-138056

However, in such a configuration, the cell culture container is taken out of an incubator. Therefore, there is a problem that the cells are stimulated by a drop in the temperature of the cells. In addition, when the cell culture container is taken out of the incubator and transported, the culture medium may be shaken. Thus, the cells may be subjected to an impact and may be peeled off or stimulated. Further, when a multilayer type culture container is used, the weight of the container is heavy, and the manual transfer of the container is not easy. Furthermore, since a liquid feeding tube is reconnected, there is a problem that the cells have to be discarded due to contamination or the like.

Therefore, in order to replace the culture medium in the incubator, it is also conceivable to adopt, for example, a configuration in which a smaller version of the configuration of Patent Document 1 is brought into the incubator. However, even in the incubator, the reconnection of a tube or the like may cause contamination due to introduction of bacteria. For this reason, at least the inside of the incubator needs to be kept in a clean atmosphere. After all, in consideration of the opening and closing of a door of the incubator, a high degree of cleanness is also required in the room where the incubator is installed.

When the tube is attached to or detached from the cell culture container in the incubator, a $CO_2$ gas or the like is also introduced into the incubator. Therefore, the gas is leaked and the room is humidified, which may cause rusting. For this reason, humidity management is also required.

Furthermore, in order to handle the multilayer type cell culture container in the incubator where there are many spatial restrictions, it is necessary to devise appropriate measures.

SUMMARY

By paying attention to such a problem, it is an object of the present disclosure to provide a novel cell culture system and a novel cell culture device that do not require a high-grade clean environment and can appropriately handle a multilayer type cell culture container despite a lot of spatial restrictions.

In order to achieve such an object, the present disclosure takes the following measures.

According to one embodiment of the present disclosure, a cell culture system includes: a cell culture container; a liquid storage part configured to store a liquid including a culture medium or a reagent to be supplied to the cell culture container; and a cell collection part configured to collect cells cultured in the cell culture container, wherein the cell culture container, the liquid storage part and the cell collection part are connected by spatially closed-system lines at least during a period from feeding of the liquid to the cell culture container to removal of the cultured cells, wherein the cell culture container is arranged in an incubator in a form of a multistage shelf including a liquid supply/discharge port, and wherein the cell culture container is posture-changeable in the incubator between a posture for distributing the liquid to each shelf through the liquid supply/discharge port while maintaining a state of the closed-system lines and a posture for collecting and discharging the liquid from each shelf through the liquid supply/discharge port.

This makes it possible to cope with mass culture by using the multistage-shelf-type cell culture container. At this time, since the cell culture container is not taken out of the incubator, the cells are not damaged by a temperature change or vibration. Since no hand technique is required, it is possible to reduce labor. In addition, since the closed system is maintained, it is possible to prevent contamination which may be caused by the introduction of bacteria. Since the incubator and hence the room need not be kept at a high degree of cleanliness, it is possible to save an operator from wearing excessive clean clothes when operating the device. Similarly, since the closed-system lines prevent the gas from being leaked into the incubator, it is not necessary to control the humidity in the incubator. Furthermore, since the number of the liquid supply/discharge ports can be reduced by distributing and collecting the liquid from the liquid supply/discharge ports for each shelf, it is possible to simplify the peripheral structure of the cell culture container which is movable in the incubator.

According to one embodiment of the present disclosure, the cell culture container includes a plurality of cell culture containers arranged in the incubator, and at least the cell culture containers are connected to each other via the closed-system lines to enable subculture of the cultured cells. Therefore, the culture rate can be substantially increased while maintaining the basic effects of the present embodiment.

According to one embodiment of the present disclosure, a cell culture device includes: a multistage-shelf-type cell culture container disposed in an incubator and including a liquid supply/discharge port; a drive mechanism configured to change a posture of the cell culture container between a posture for distributing a liquid to each shelf through the liquid supply/discharge port and a posture for collecting the liquid from each shelf and discharging the liquid through the liquid supply/discharge port; and a liquid supply/discharge tube configured to be kept connected to the liquid supply/discharge port while driving the cell culture container.

This makes it possible to perform appropriate handling of the cell culture container while reducing, as far as possible, the number of liquid supply/discharge tubes which are movable in a state in which the tubes are connected to the cell culture container.

Further, the liquid supply/discharge port includes a liquid supply port and a liquid discharge port. As long as the liquid supply/discharge port serves as a liquid supply port for supplying a liquid to each shelf and a liquid discharge port for discharging the liquid from each shelf and as long as the drive mechanism drives the cell culture container so that a posture of the cell culture container when the liquid is supplied is different from a posture of the cell culture container when the liquid is discharged, it is possible to further reduce the number of ports and the number of tubes.

According to one embodiment of the present disclosure, the cell culture container includes a communication portion corresponding to each of shelf spaces at a side of one end edge of each shelf constituting a multistage shelf structure, wherein the shelf spaces are partitioned from each other in portions other than the communication portion, wherein the one end edge is provided with an upstanding wall for storing the liquid on a shelf surface when the shelf is horizontal, and wherein the drive mechanism is configured to drive the cell culture container to sequentially take a liquid supply posture in which each shelf surface is erected so that the communication portion is positioned downward and the liquid is uniformly introduced to each shelf, an intermediate posture in which the liquid in each shelf space is separated by rotating the cell culture container from the liquid supply posture so that the communication portion is positioned upward, and a culture posture in which the liquid is equally distributed on each shelf surface by subsequently rotating the cell culture container so that the shelf surface of each shelf is horizontal.

If the liquid supply posture is directly shifted to the culture posture, an unequal state in which it is easier for the liquid to enter the lower shelf and it is more difficult for the liquid to enter the upper shelf may be established over time. Therefore, the cell culture container has to be rapidly rotated to prevent such a state. For this reason, there is a possibility that the cells may be damaged, and there is a concern that the cells may be dried. On the other hand, if the intermediate posture as described above is interposed, even when the cell culture container is not suddenly rotated, the liquid is evenly distributed in the respective shelf spaces without creating a vertical relationship on the shelf from the liquid supply posture to the intermediate posture. Therefore, even if the subsequent rotation from the intermediate posture to the culture posture is not suddenly performed, the liquid that has entered the respective shelf spaces can be brought into to a state in which the liquid is stored on the horizontal shelf surface as it is. As a result, the posture of the cell culture container can be changed at an appropriate speed, the damage to the cells can be reduced, and the cells can be prevented from drying.

According to one embodiment of the present disclosure, the drive mechanism includes: a first driver configured to rotationally drive the cell culture container about a first axis; a second driver configured to rotationally drive the cell culture container about a second axis orthogonal to the first axis; and a controller configured to control the first driver and the second driver, wherein the first driver is positioned in a direction extending along the first axis, and wherein the second driver is disposed in a vicinity of the first driver and is connected to the second axis via a transmission part configured to transmit power to the second axis along a direction parallel to the first axis.

By doing so, at least the drive mechanism is not bulky in the second axial direction. Therefore, the drive mechanism can be appropriately disposed in the incubator having a large spatial restriction.

Furthermore, if the cell culture container whose posture is changed with the liquid supply/discharge tube kept in a connected state is further provided with an automatic winding mechanism that winds up the extra length with a certain tension applied to the liquid supply/discharge tube, even when the cell culture container is rotated with the liquid supply/discharge tube kept in a connected state, it is possible to effectively prevent the liquid supply/discharge tube from being entangled with the surroundings.

BRIEF DESCRIPTION OF DRAWINGS

The accompanying drawings, which are incorporated in and constitute a part of the specification, illustrate embodiments of the present disclosure, and together with the general description given above and the detailed description of the embodiments given below, serve to explain the principles of the present disclosure.

FIG. 1 is a schematic configuration diagram of a cell culture system according to an embodiment of the present disclosure.

FIG. 2 is a view showing an incubator of the system which accommodates cell culture containers.

FIGS. 3A and 3B are views showing a shelf structure of a cell culture container.

FIGS. 9A and 9B are views showing a procedure for driving the cell culture container.

FIG. 12 is a view showing a modification of the present disclosure.

DETAILED DESCRIPTION

Figure 3B:
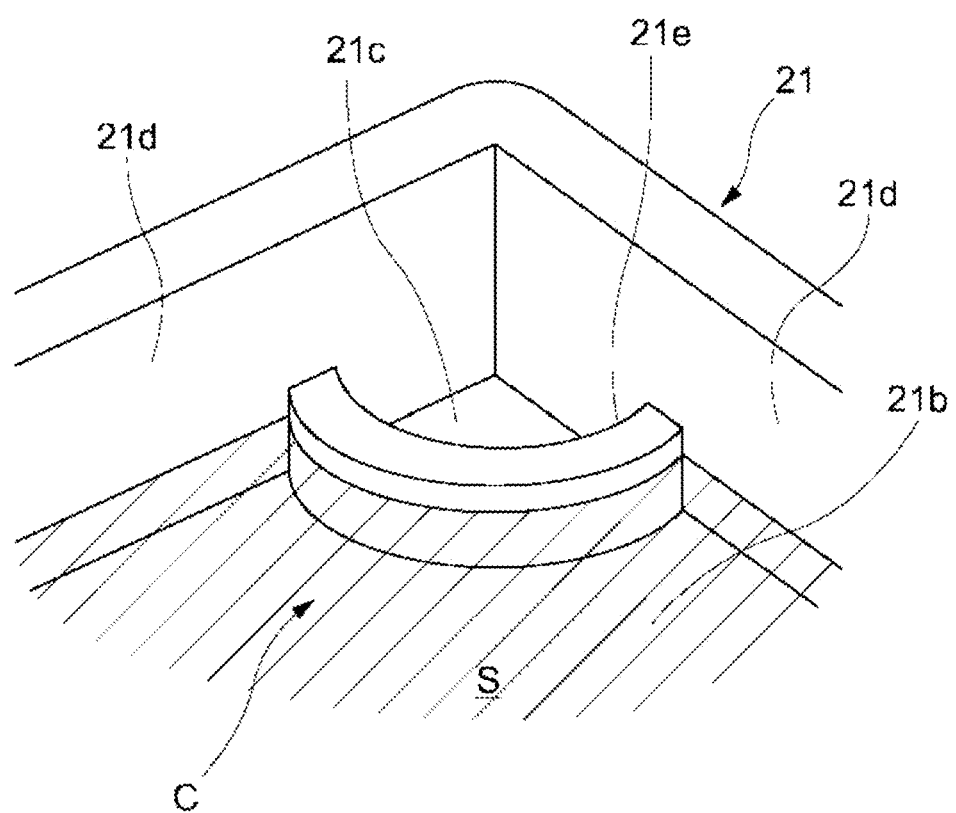
Figure 4:
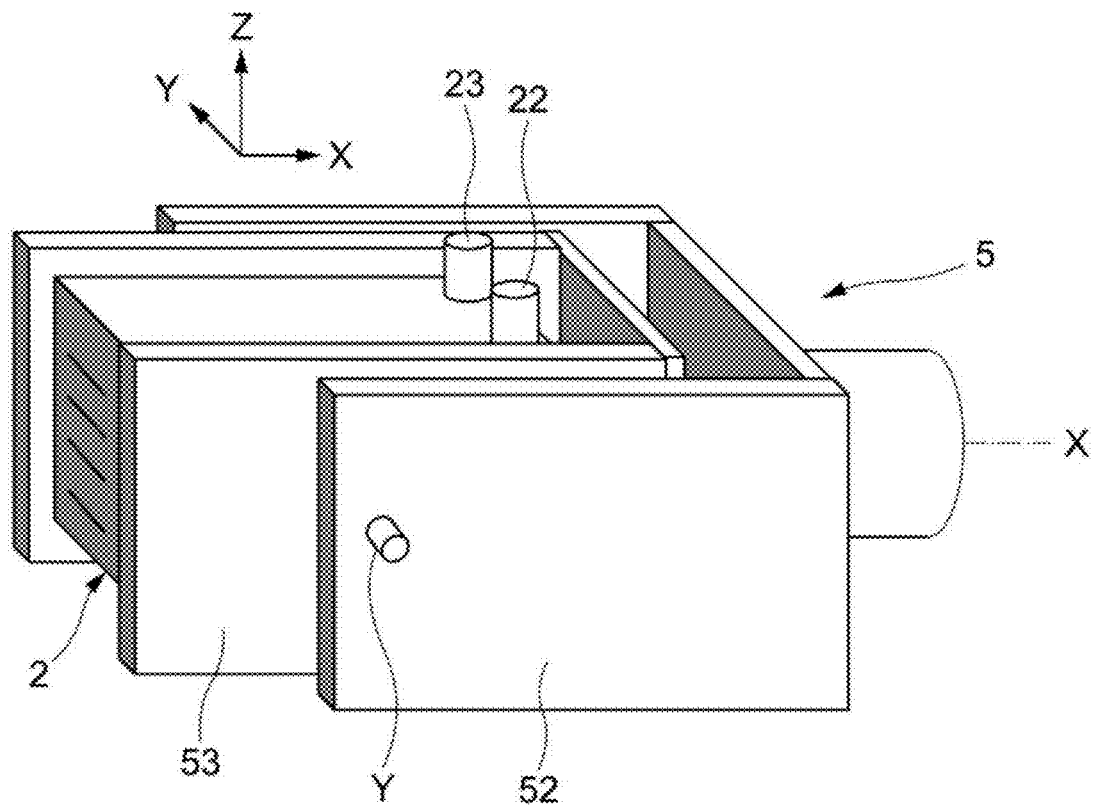
FIG. 4 is a view showing the cell culture container together with a drive mechanism.
Figure 5:
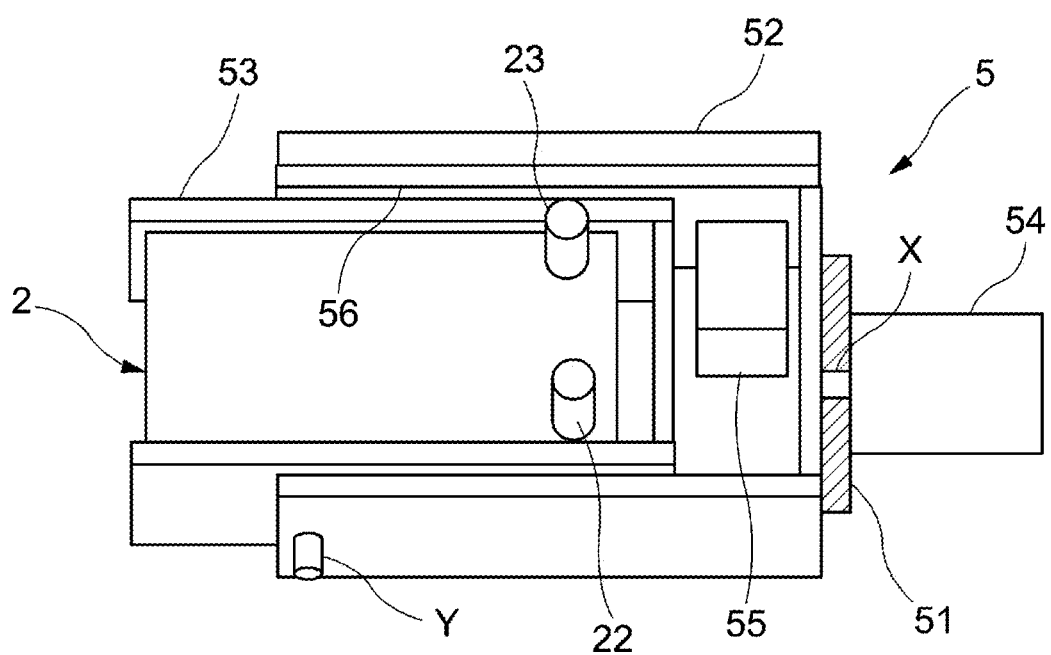
FIG. 5 is a view showing the cell culture container together with the drive mechanism.

Reference will now be made in detail to various embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, systems, and components have not been described in detail so as not to unnecessarily obscure aspects of the various embodiments.

Hereinafter, embodiments of the present disclosure will be described with reference to the drawings.

FIG. 1 is a system diagram schematically showing a cell culture system CCS according to the present embodiment. This cell culture system CCS includes a cell culture container 2 (2(A), 2(B)), a refrigerator 1 serving as a liquid storage part for storing liquids such as a culture medium and various reagents to be supplied to the cell culture container 2, and a cell collection part 3 for collecting cells cultured in the cell culture container 2. Appropriate portions of the cell culture container 2, the refrigerator 1, and the cell collection part 3 are connected by sterile connectors (not shown). After the cell culture container 2, the refrigerator 1, and the cell collection part 3 are assembled, the inside of the system is configured by closed lines L from the start of an operation to the end of the operation, whereby the entry of bacteria from the outside is prevented.

The refrigerator 1 is maintained at a temperature required to keep a culture medium and various reagents cold, for example, about 5 degrees C.

The cell culture container 2 has a shelf structure for culturing cells in a flatly spread culture medium. The cell culture container 2 is placed in a temperature environment of about 37 degrees C. to promote cell division.

The cell collection part 3 collects the cells in the liquid taken out after culturing in the cell culture container 2. Between the cell culture container 2 and the cell collection part 3, an intermediate processing part IP such as an analysis part for analyzing the state of the cells and an adjustment part for adjusting the dilution of the suspension containing the cells may be interposed as necessary. All the lines in the intermediate processing part IP are also configured by closed lines L.

In such closed-system lines L, there is constructed a system that automatically performs, without human intervention, a step of preparing liquids such as a culture medium and a reagent in the refrigerator 1 and feeding those liquids from the refrigerator 1 to the cell culture container 2, a step of culturing cells in the cell culture container 2, a step of taking out the cultured cells from the cell culture container 2 and collecting the cultured cells in the cell collection part 3, a step for causing the intermediate processing part IP to perform various intermediate processes on the liquids taken out from the cell culture container 2 before collection, and the like.

For this purpose, valves V and pumps P (a pressure feed pump P(a) and a suction pump P(b)) are connected to the respective lines L as necessary. These valves V and pumps P are controlled by a control command SG from a controller CT.

In the present embodiment, in order to maintain the cell culture container 2 at a predetermined temperature without breaking the closed-system lines L, a cell culture device CV including the cell culture container 2 and peripheral component parts is arranged in the incubator 4 as shown in FIGS. 1 and 2 while connecting a liquid supply/discharge tube 61 that constitutes a part of the closed-system lines L.

Thus, the cell culture container 2 receives a spatial restriction. For that reason, in order to enable culture as much as possible, it is necessary to increase the culture rate in the cell culture container 2.

Therefore, the present embodiment adopts a configuration in which the cell culture container 2 is formed in a multistage shelf structure to increase the culture area just as much as the number of shelves 21. Due to the multistage shelf structure, there is a need for a process of spreading the liquid supplied from the outside to the respective shelves 21 and discharging the liquid from the respective shelves 21 to the outside after the culture is completed. At this time, in order to reduce the number of closed-system lines L to be connected as much as possible, a liquid supply/discharge port 22 serving as both a liquid supply port and a liquid discharge port is provided in a housing of the cell culture container 2. The liquid supply/discharge port 22 is common to the respective shelves 21. By changing the posture of the cell culture container 2 while maintaining the closed line state in the incubator 4, it is possible to perform the liquid supply to the respective shelves 21 and the liquid discharge from the respective shelves 21.

Specifically, as shown in FIGS. 3A and 3B, in the cell culture container 2, communication portions 21c are provided in corners C on the side of one end edge 21a of each shelf 21 by partially cutting out a shelf surface 21b so that a liquid can evenly enter the respective shelf spaces S. The shelf spaces S are configured to be partitioned by the shelf surface 21b and the side surface 21d in the portions other than the communication portion 21c. An upstanding wall 21e having a lower height than the side surface 21d is provided at a boundary between the communication portion 21c and the shelf surface 21b so that the liquid can be stored when the shelf surface 21b is kept in a horizontal state and the liquid can be discharged when the shelf surface 21b is inclined or inverted. That is, the hatched portion in FIG. 3B indicates a region where the liquid can be stored when the shelf surface 21b is horizontal.

As shown in FIGS. 4 to 7, the cell culture device CV includes a drive mechanism 5 for changing the posture of the cell culture container 2.

The drive mechanism 5 includes a base 51, a turntable 52 attached to the base 51 so as to be rotatable about a first axis X, a container holding member 53 attached to the turntable 52 so as to be rotatable about a second axis Y, a first drive part (driver) 54 configured to rotationally drive the turntable 52 about the first axis X, a second drive part (driver) 55 configured to rotationally drive the container holding member 53 about the second axis Y, and the controller CT as a control part for controlling the drive parts 54 and 55. The cell culture container 2 can be detachably attached to the container holding member 53 via a clamping part 53a that makes use of an elastic force.

The first drive part 54 is positioned in the direction extending along the first axis X from the cell culture container 2. The second drive part 55 is disposed in the vicinity of the first drive part 54 and is connected to the second axis Y via a transmission mechanism 56 (see FIG. 7) that makes use of a belt, a chain or the like configured to transmit power to the second axis Y along the first axis X.

Figure 6:
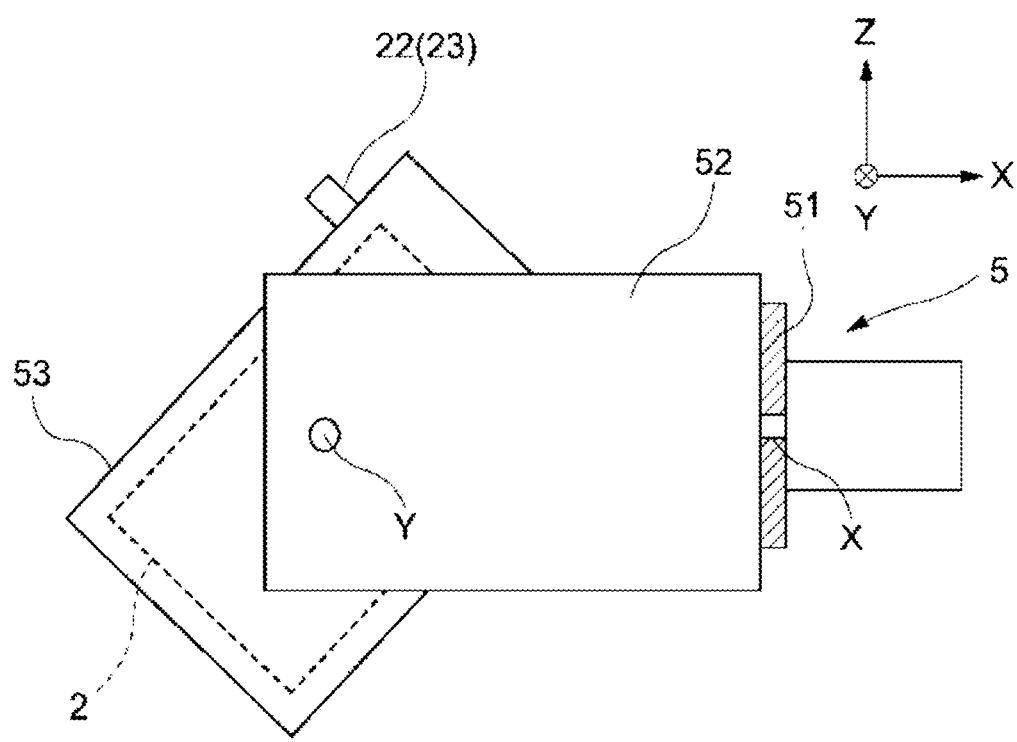
FIG. 6 is a view showing the cell culture container together with the drive mechanism.
Figure 7:
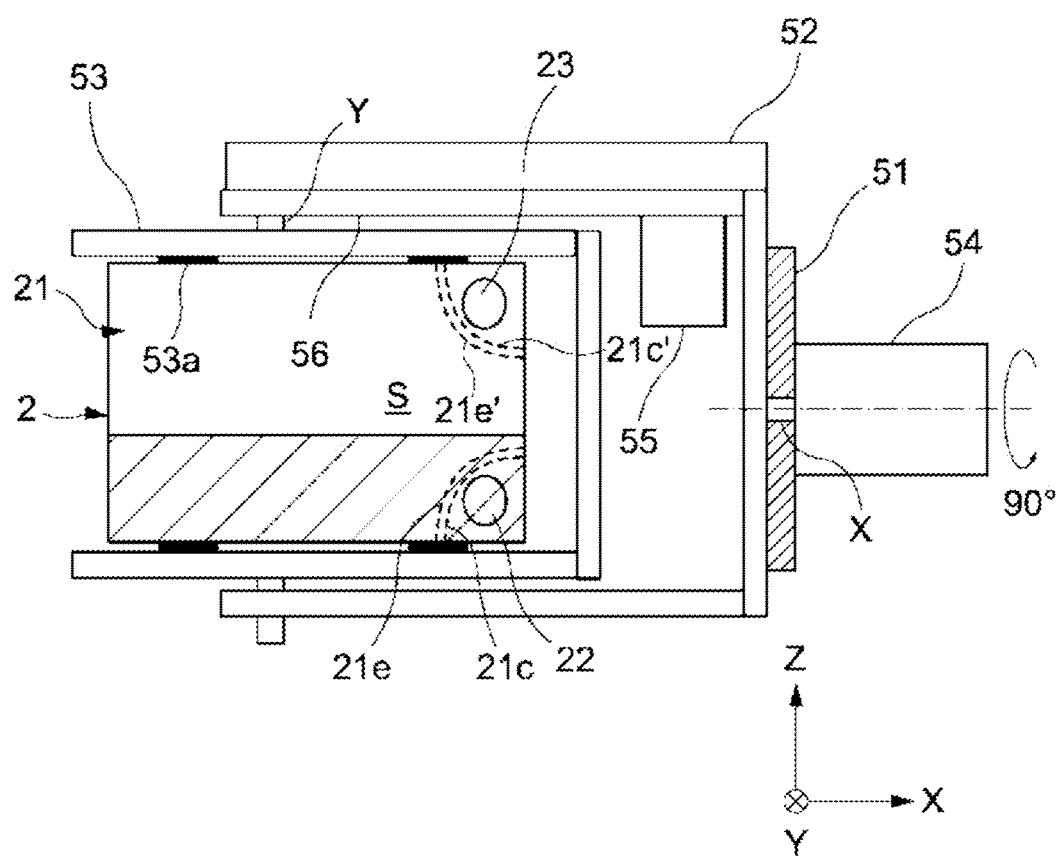
FIG. 7 is a view showing a procedure for driving the cell culture container.

That is, if only the first drive part 54 is driven, as shown in FIG. 7, the turntable 52, the container holding member 53, and the cell culture container 2 can rotate about the first axis X. If the only the second drive part 55 is driven, as shown in FIG. 6, the turntable 52 does not rotate but the container holding member 53 and the cell culture container 2 can rotate about the second axis Y. If the first drive part 54 and the second drive part 55 are driven simultaneously, the turntable 52, the container holding member 53, and the cell culture container 2 can rotate about the first axis X as shown in FIG. 7 while the container holding member 53 and the cell culture container 2 can rotate about the second axis Y as shown in FIG. 6. The drive mechanism 5 may control the posture of the cell culture container 2 by open control, or may feedback control the posture of the cell culture container 2 by providing a sensor or the like for detecting the posture of the shelf surface 21b.

When the cell culture container 2 is swung, it is necessary to rotate the cell culture container 2 at a speed at which the culture medium is not shaken and excessive stimulation is not applied to the cells, and it is necessary to supply the liquid evenly to the respective shelves 21. Therefore, posture control is performed according to the following procedure.

First, the controller CT of FIG. 1 for driving the drive parts 54 and 55 drives the first drive part 54 to rotate the cell culture container 2 about the first axis X by 90 degrees so that the communication portion 21c is positioned downward as shown in FIG. 7. Each shelf surface 21b is erected to obtain a liquid supply posture. Then, the liquid is supplied from the front side to the back side in FIG. 7 with respect to the liquid supply/discharge port 22 facing in the horizontal direction, thereby allowing the liquid to evenly enter the respective shelf spaces S. At this stage, the liquid can be moved between the shelf spaces S when the posture of the cell culture container 2 is changed.

Figure 8A:
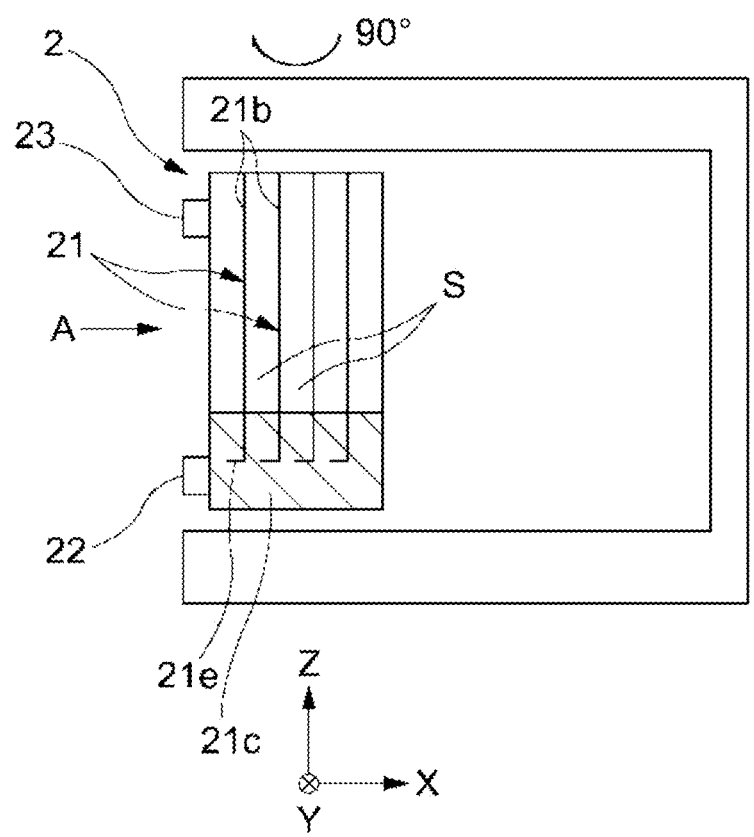
FIGS. 8A and 8B are views showing a procedure for driving the cell culture container.
Figure 8B:
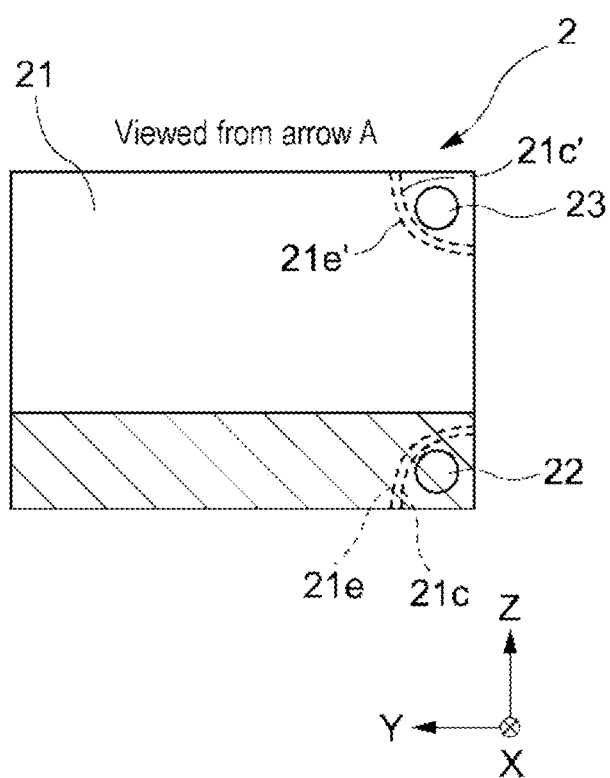

In this state, the second drive part 55 is driven to rotate the cell culture container 2 about the second axis Y by 90 degrees (see FIGS. 8A and 8B), and the first drive part 54 is driven to rotate the cell culture container 2 about the first axis X by 90 degrees (see FIGS. 9A and 9B), thereby bringing the cell culture container 2 into an intermediate posture. Thus, the communication portion 21c is located upward, and the liquid is substantially equally distributed in the respective shelf spaces S. At this stage, the liquid that has entered each shelf space S cannot move back and forth even if the posture of the cell culture container 2 is changed.

Figure 10A:
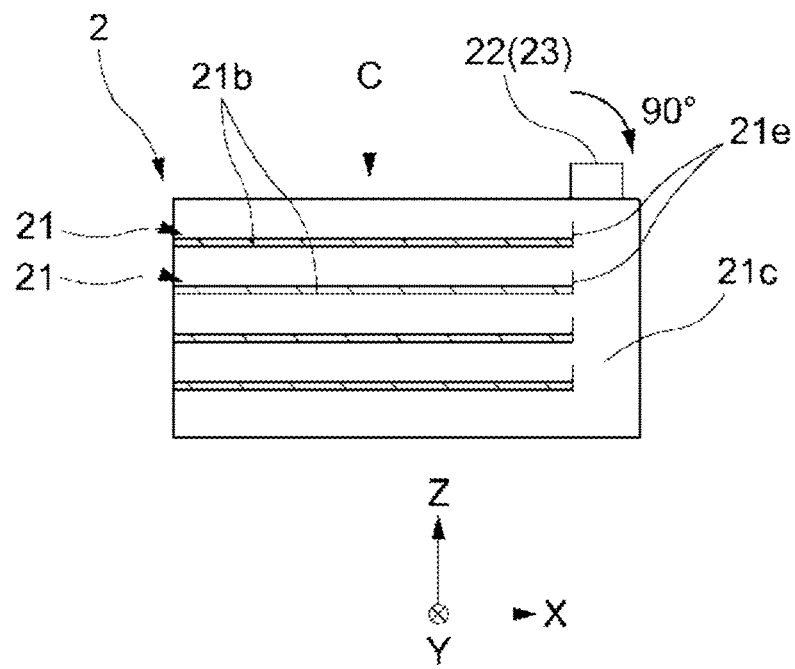
FIGS. 10A and 10B are views showing a procedure for driving the cell culture container.
Figure 10B:
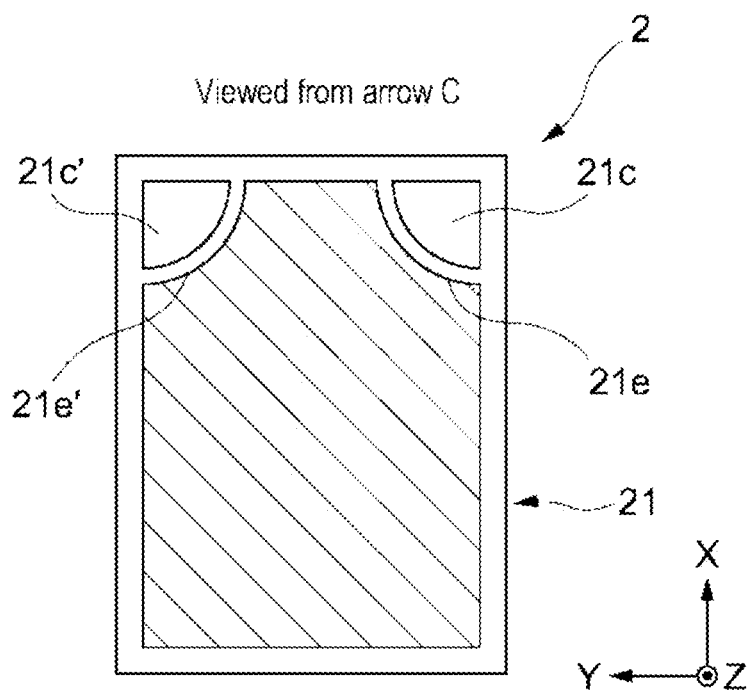

Furthermore, the second drive part 55 is driven to rotate the cell culture container about the second axis Y by 90 degrees, thereby bringing each shelf surface 21b into a horizontal culture posture so that the liquid is substantially evenly distributed on the respective shelf surfaces 21b (see FIGS. 10A and 10B). The liquid is stored in the region indicated by hatching in FIG. 10B. Culture proceeds in this state.

Figure 11A:
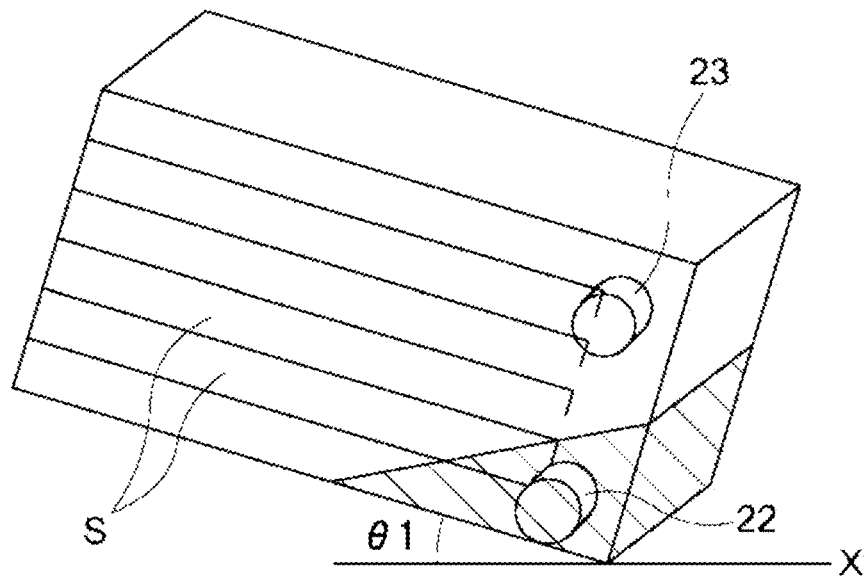
FIGS. 11A and 11B are views showing a procedure for driving the cell culture container.
Figure 11B:
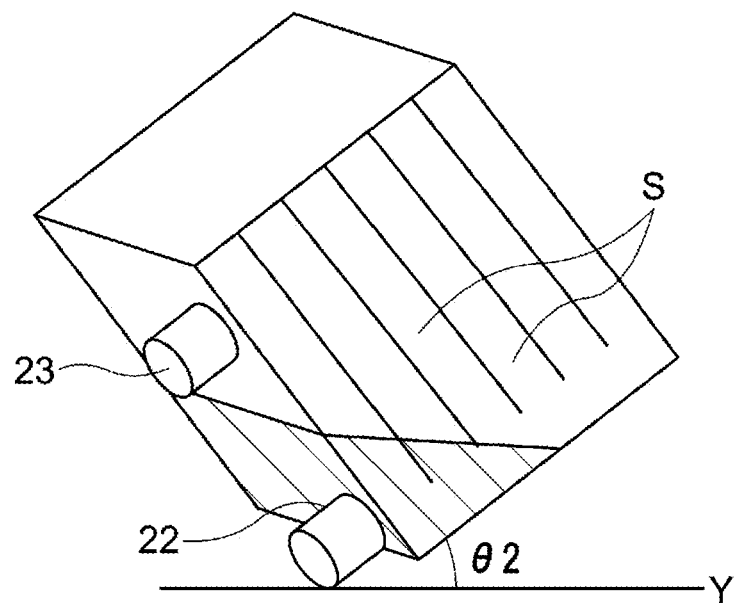

At the time of liquid discharge, as shown in FIGS. 11A and 11B, the first drive part 54 is driven about the first axis X so as to be held at an angle θ1 with respect to the horizontal direction and the second drive part 55 is driven about the second axis Y so as to be held at an angle θ2 with respect to the horizontal direction (liquid discharge posture) so that the liquid supply/discharge port 22 faces downward and the liquid in each shelf space S reaches the liquid supply/discharge port 22 through the communication portion 21c. The angles θ1 and θ2 are set to, for example, about 30 degrees so that no liquid remains.

When the liquid discharge is completed, the posture returns to the posture shown in FIG. 7 for the next liquid supply.

The controller CT shown in FIG. 1 incorporates sequences regarding the driving performed by such series of drive parts 54 and 55, the control of the pumps P (P(a) and P(b)) for liquid supply and discharge, the control of the valves V at the respective portions, and the like.

During culture, it is necessary to replace the culture medium at a predetermined frequency (for example, once a day). Further, as shown in FIGS. 1 and 2, a plurality of (two in the illustrated example) cell culture containers 2(A) and 2(B) may be installed in the incubator 4, and the drive mechanism 5 and the liquid supply/discharge tube 61 may be connected to each of the cell culture containers 2(A) and 2(B). So-called subculture in which the cells cultured in the first cell culture container are transferred to the second cell culture container for further growth may be performed. For this reason, the controller CT shown in FIG. 1 also incorporates a sequence for replacing the culture medium for each of the cell culture containers 2(A) and 2(B), a sequence for peeling off the cells cultured in the first cell culture container 2(A), discharging the cells from the liquid supply/discharge port 22 and introducing the cells into the second cell culture container 2(B) through the liquid supply/discharge port 22, and the like.

Furthermore, what is indicated by reference numeral 23 in each figure is an air supply/exhaust port. When supplying the liquid through the liquid supply/discharge port 22, the internal gas is extracted from the cell culture container. When discharging the liquid through the liquid supply/discharge port 22, the gas is introduced into the cell culture container, thereby smoothly performing the liquid supply and discharge. What is indicated by reference numeral 62 is an air supply/exhaust tube. The liquid supply/discharge port 22 is moved in and out from the bottom of the cell culture container 2 to prevent gas bubbles from being mixed into the liquid.

In a series of operations, in order to prevent the liquid supply/discharge tube 61 or the air supply/exhaust tube 62 from being entangled, the driving of the cell culture container 2 by the drive parts 54 and 55 is controlled so that the liquid supply/discharge tube 61 or the air supply/exhaust tube 62 is not rotated by 180 degrees or more about the X axis and Y axis as far as possible. What is indicated by reference numeral 21c' in the figure is a communication portion provided by cutting out each shelf surface 21b and communicating with the air supply/exhaust port 23. What is indicated by reference numeral 21e' in the figure is an upstanding wall for storing a liquid on each shelf surface 21b.

As described above, the cell culture system CCS of the present embodiment includes: a cell culture container 2; a refrigerator 1 serving as a liquid storage part for storing a liquid such as a culture medium or a reagent to be supplied to the cell culture container 2; and a cell collection part 3 configured to collect cells cultured in the cell culture container 2, wherein the cell culture container 2, the refrigerator 1, and the cell collection part 3 are connected by spatially closed-system lines L at least during a period from the feeding of the liquid to the cell culture container 2 to the removal of the cultured cells, the cell culture container 2 is arranged in an incubator 4 in the form of a multistage shelf having a liquid supply/discharge port 22, and the cell culture container 2 is posture-changeable in the incubator 4 between a posture for distributing the liquid to each shelf 21 through the liquid supply/discharge port 22 while maintaining a closed line state and a posture for collecting and discharging the liquid from each shelf 21 through the liquid supply/discharge port 22.

This makes it possible to cope with mass culture by using the multistage-shelf-type cell culture container 2. At this time, since the cell culture container 2 is not taken out of the incubator 4, the cells are not damaged by a temperature change or vibration. Since no technique is required, it is possible to reduce labor. In addition, since the closed system is maintained, it is possible to prevent contamination which may be caused by the introduction of bacteria. Since the incubator 4 and hence the room need not be kept at a high degree of cleanliness, it is possible to save the operator from wearing excessive clean clothes when operating the device. Similarly, since the closed-system lines L prevent the gas from being leaked into the incubator 4, it is not necessary to control the humidity in the incubator 4. Furthermore, since the number of the liquid supply/discharge ports 22 can be reduced by distributing and collecting the liquid from the liquid supply/discharge ports 22 for each shelf 21, it is possible to simplify the peripheral structure of the cell culture container 2 which is movable in the incubator 4.

In addition, the cell culture container 2 includes a plurality of cell culture containers 2(A) and 2(B) arranged in the incubator 4, and at least the cell culture containers 2(A) and 2(B) are connected to each other via the closed-system lines L so as to enable subculture of the cultured cells. Therefore, the culture rate can be greatly increased while maintaining the basic effects of the present embodiment.

Further, the cell culture device CV of the present embodiment includes: a multistage-shelf-type cell culture container 2 disposed in an incubator 4 and having a liquid supply/discharge port 22; a drive mechanism 5 configured to change a posture of the cell culture container 2 between a posture for distributing a liquid to each shelf 21 through the liquid supply/discharge port 22 and a posture for collecting the liquid from each shelf 21 and discharging the liquid through the liquid supply/discharge port 22; and a liquid supply/discharge tube 61 configured to be kept connected to the liquid supply/discharge port 22 during the driving thereof. This makes it possible to perform appropriate handling of the cell culture container 2 while reducing, as far as possible, the number of liquid supply/discharge tubes 61 which are movable in a state in which the tubes are connected to the cell culture container 2.

In a configuration (not shown), the liquid supply/discharge port 22 may be configured by a liquid supply port and a liquid discharge port, and a liquid supply tube and a liquid discharge tube may be connected to the liquid supply port and the liquid discharge port, respectively. However, in the present embodiment, the liquid supply/discharge port 22 serves as a liquid supply port configured to supply the liquid to each shelf 21 and a liquid discharge port configured to discharge the liquid from each shelf 21, and the drive mechanism 5 is configured to drive the cell culture container 2 so that a posture of the cell culture container when the liquid is supplied is different from a posture of the cell culture container when the liquid is discharged. This makes it possible to reduce the number of ports and the number of tubes.

In that case, the cell culture container 2 includes a communication portion 21c corresponding to each of shelf spaces S on the side of one end edge 21a of each shelf constituting a multistage shelf structure, the shelf spaces S are partitioned from each other in portions other than the communication portion 21c, the cell culture container 2 is provided at one end edge 21a with an upstanding wall 21e for storing the liquid on a shelf surface 21b when the shelf 21 is horizontal, and the drive mechanism 5 is configured to drive the cell culture container 2 so as to sequentially take a liquid supply posture (see FIG. 7) in which each shelf 21 is erected so that the communication portion 21c is positioned downward and the liquid is uniformly introduced onto each shelf surface 21b, an intermediate posture (see FIGS. 9A and 9B) in which the liquid in each shelf space S is separated by rotating the cell culture container 2 from the liquid supply posture so that the communication portion 21c is positioned upward, and a culture posture (see FIGS. 10A and 10B) in which the liquid is substantially equally distributed on each shelf surface 21b by subsequently rotating the cell culture container 2 so that the shelf surface 21b of each shelf 21 is horizontal.

That is, if the cell culture container 2 is rotated about the first axis X to directly shift the liquid supply posture shown in FIG. 7 to the culture posture shown in FIGS. 10A and 10B, an unequal state in which it is easier for the liquid to enter the lower shelf 21 and it is more difficult for the liquid to enter the upper shelf 21 may be established over time. Therefore, the cell culture container 2 has to be rapidly rotated to prevent such a state. For this reason, there is a possibility that the cells may be damaged. On the other hand, if the intermediate posture as described above is interposed, even when the cell culture container 2 is not suddenly rotated, the liquid is evenly distributed in the respective shelf spaces S without creating a vertical relationship on the shelf 21 from the liquid supply posture shown in FIG. 7 to the intermediate posture shown in FIGS. 9A and 9B. Therefore, even if the subsequent rotation from the intermediate posture to the culture posture is not suddenly performed, the liquid that has entered the respective shelf spaces S can be brought into a state in which the liquid is stored on the horizontal shelf surface 21b as it is. As a result, the posture of the cell culture container 2 can be changed at an appropriate speed, and the damage to the cells can be reduced.

In addition, the drive mechanism 5 includes a first drive part 54 configured to rotationally drive the cell culture container 2 about a first axis X, a second drive part 55 configured to rotationally drive the cell culture container 2 about a second axis Y orthogonal to the first axis X, and a controller CT as a control part for controlling the drive parts 54 and 55, wherein the first drive part 54 is positioned in a direction extending along the first axis X, and the second drive part 55 is disposed in the vicinity of the first drive part 54 and is connected to the second axis Y via the transmission mechanism 56 configured to transmit power to the second axis Y along a direction parallel to the first axis X. Since at least the drive mechanism 5 is not bulky in the second axis Y direction, the drive mechanism 5 can be appropriately disposed in the incubator 4 having a large spatial restriction.

Although one embodiment of the present disclosure has been described above, the specific configuration of each part is not limited only to the embodiment described above.

For example, as shown in FIG. 12, the cell culture device may further include an automatic winding mechanism 7 configured to wind up an extra length of the liquid supply/discharge tube 61 while applying a certain tension to the liquid supply/discharge tube 61 with respect to the cell culture container 2 whose posture is changed in a state in which the liquid supply/discharge tube 61 is connected thereto.

According to this configuration, the liquid supply/discharge tube 61 does not sag and does not become entangled with the surroundings. Furthermore, since the liquid supply/discharge tube 61 does not sag, it is possible to eliminate the liquid which may otherwise remain in the sagging portion of the liquid supply/discharge tube 61. For example, the automatic winding mechanism 7 may be of a type in which the liquid supply/discharge tube 61 is wound around a rotation mechanism provided with an actuator, and the actuator of the rotation mechanism is rotated in the forward or reverse direction depending on the swing angle of the cell culture container 2 to take in or take out the liquid supply/discharge tube 61 so that the liquid supply/discharge tube 61 can maintain a constant tension at any angle of the cell culture container 2.

Furthermore, the liquid supply/discharge port and the liquid supply/discharge tube may be divided into one for liquid supply and one for liquid discharge.

Furthermore, the configuration of the drive mechanism and the procedure for changing the posture of the cell culture container may be other configurations and procedures as long as they can pass through the intermediate posture.

Furthermore, in the above-described embodiment, the refrigerator 1 as a liquid storage part is disposed outside, and the liquid in the refrigerator 1 is directly supplied to the cell culture containers 2 (2(A) and 2(B)) in the incubator 4. Alternatively, as shown in FIGS. 13A and 13B, a bag 101 as a liquid storage part may be disposed so as to be suspended in the incubator 4, and the liquid may be supplied from the bag 101 to the cell culture containers 2 (2(A) and 2(B)).

Figure 13A:
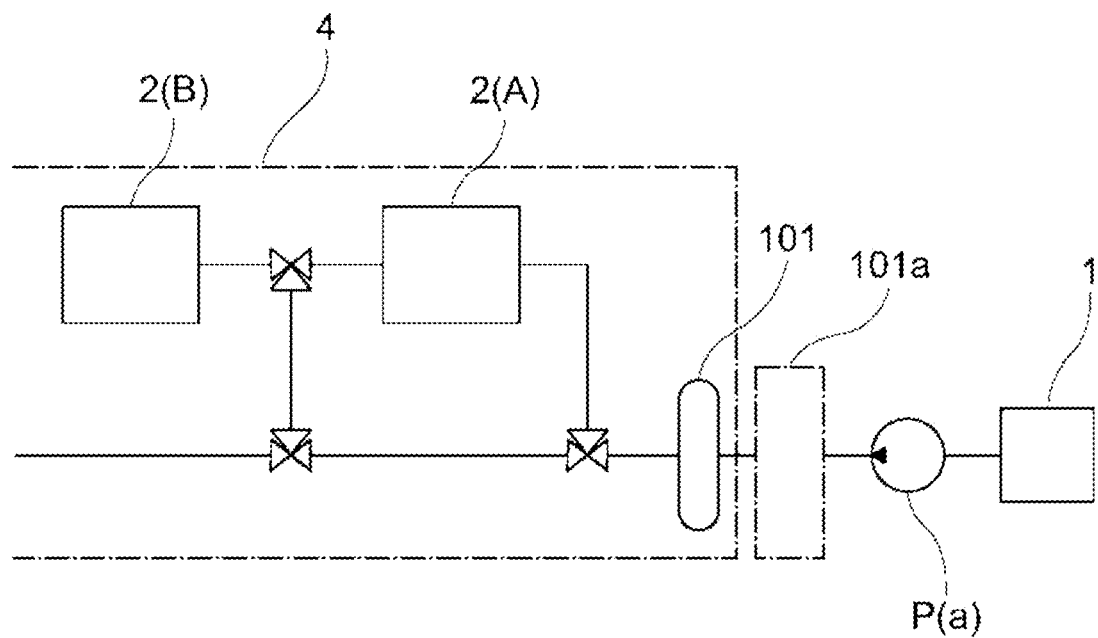
FIGS. 13A and 13B are views showing other modifications of the present disclosure.
Figure 13B:
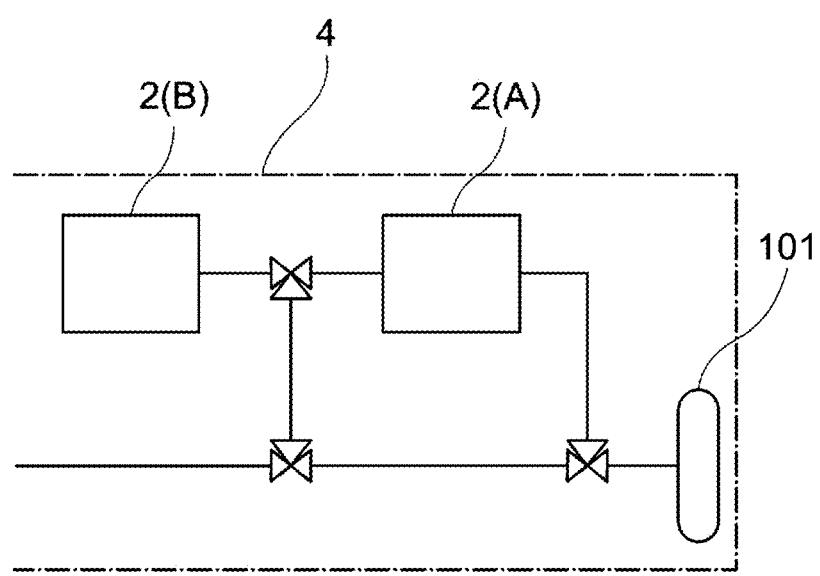

In this case, as shown in FIG. 13A, the liquid from the refrigerator 1 may be temporarily accumulated in the bag 101 and then supplied to the cell culture containers 2 (2(A) and 2(B)). Alternatively, as shown in FIG. 13B, the liquid may be merely supplied from the bag 101 without going through the external refrigerator 1.

In the configuration of FIG. 13A, it is also effective to provide a preheating part 101a for preheating the liquid before being introduced into the incubator 4. If a low temperature solution is put into the cell culture containers 2 (2(A) and 2(B)) without preheating the same, there is a risk of irritating the cells. However, if a solution is preheated in advance, it is possible to prevent the temperature in the incubator 4 from fluctuating and to appropriately perform the temperature control in the incubator 4.

Of course, it is effective to apply such a preheating part 101a to the configuration shown in FIG. 1. It is possible to optimize the temperature control by preheating the liquid before being introduced into the incubator 4.

Of course, it may be possible to adopt a configuration in which the liquid introduced into the incubator 4 is heated in the incubator 4 and supplied to the cell culture containers 2 (2(A) and 2(B)).

Other configurations and various modifications may be adopted without departing from the spirit of the present disclosure.

According to the present disclosure having the aforementioned configuration, it is possible to provide a novel useful cell culture system and a novel useful cell culture device that do not require a high-grade clean environment and can appropriately handle a multistage-shelf-type cell culture container despite a lot of spatial restrictions.

While certain embodiments have been described, these embodiments have been presented by way of example only, and are not intended to limit the scope of the disclosures. Indeed, the embodiments described herein may be embodied in a variety of other forms. Furthermore, various omissions, substitutions and changes in the form of the embodiments described herein may be made without departing from the spirit of the disclosures. The accompanying claims and their equivalents are intended to cover such forms or modifications as would fall within the scope and spirit of the disclosures.

What is claimed is:

1. A cell culture system, comprising:
a plurality of cell culture containers, each of which includes a liquid supply/discharge port and is configured as a multistage shelf, the plurality of cell culture containers being disposed in an incubator, wherein at least the cell culture containers are directly connected to each other via spatially closed-system lines to enable subculture of cells cultured in the cell culture containers between the cell culture containers;
a driver configured to change a posture of each of the cell culture containers between a posture for distributing a liquid to each shelf through the liquid supply/discharge port and a posture for collecting and discharging the liquid from each shelf through the liquid supply/discharge port while the connection of the cell culture containers to each other via the closed-system lines is maintained, wherein the driver includes:
a first driver configured to rotate each of the cell culture containers about a first axis, and positioned in a direction extending along the first axis from each of the cell culture containers; and
a second driver configured to rotate each of the cell culture containers about a second axis orthogonal to the first axis, disposed in a vicinity of the first driver, and connected to the second axis via a transmission part configured to transmit power to the second axis along a direction parallel to the first axis; and
a liquid storage configured to store a liquid including a culture medium or a reagent to be supplied to the cell culture containers,
wherein the cell culture containers and the liquid storage are connected by the closed-system lines at least during a period from feeding of the liquid to the cell culture containers to removing cultured cells out of the cell culture containers.

2. A cell culture device, comprising:
a plurality of multistage shelf cell culture containers, each of which includes a liquid supply/discharge port, the plurality of multistage shelf cell culture containers being disposed in an incubator, wherein at least the cell culture containers are directly connected to each other via spatially closed-system lines to enable subculture of cells cultured in the cell culture containers between the cell culture containers;
a driver configured to change a posture of each of the cell culture containers between a posture for distributing a liquid to each shelf through the liquid supply/discharge port and a posture for collecting and discharging the liquid from each shelf through the liquid supply/discharge port while the connection of the cell culture containers to each other via the closed-system lines is maintained, wherein the driver includes:
a first driver configured to rotate each of the cell culture containers about a first axis, and positioned in a direction extending along the first axis from each of the cell culture containers; and
a second driver configured to rotate each of the cell culture containers about a second axis orthogonal to the first axis, disposed in a vicinity of the first driver, and connected to the second axis via a transmission part configured to transmit power to the second axis along a direction parallel to the first axis; and a liquid supply/discharge tube configured to be kept connected to the liquid supply/discharge port while driving each of the cell culture containers.

3. The device of claim 2, wherein the liquid supply/discharge port serves as a liquid supply port configured to supply the liquid to each shelf and a liquid discharge port configured to discharge the liquid from each shelf, and the driver is configured to drive each of the cell culture containers so that a posture of each of the cell culture containers when the liquid is supplied is different from a posture of each of the cell culture containers when the liquid is discharged.

4. The device of claim 3, wherein each of the cell culture containers includes a communication portion corresponding to each of shelf spaces at a side of one end edge of each shelf constituting a multistage shelf structure,
 wherein the shelf spaces are partitioned from each other in portions other than the communication portion,
 wherein the one end edge is provided with an upstanding wall for storing the liquid on a shelf surface when the shelf is horizontal, and
 wherein the driver is configured to drive each of the cell culture containers to sequentially take a liquid supply posture in which each shelf surface is erected so that the communication portion is positioned downward and the liquid is uniformly introduced to each shelf, an intermediate posture in which the liquid in each shelf space is separated by rotating each of the cell culture containers from the liquid supply posture so that the communication portion is positioned upward, and a culture posture in which the liquid is equally distributed on each shelf surface by subsequently rotating each of the cell culture containers so that the shelf surface of each shelf is horizontal.

5. The device of claim 2, wherein a controller is configured to control the first driver and the second driver.

6. The device of claim 2, further comprising:
 an automatic winder configured to wind up an extra length of the liquid supply/discharge tube while applying a certain tension to the liquid supply/discharge tube with respect to each of the cell culture containers whose posture is changed in a state in which the liquid supply/discharge tube is connected to each of the cell culture containers.

* * * * *